United States Patent [19]

Mark et al.

[11] 4,242,527

[45] Dec. 30, 1980

[54] PROCESS FOR PURIFYING CRUDE DIPHENOLS

[75] Inventors: Victor Mark, Evansville; Charles V. Hedges, Mt. Vernon, both of Ind.

[73] Assignee: General Electric Company, Pittsfield, Mass.

[21] Appl. No.: 41,642

[22] Filed: May 23, 1979

Related U.S. Application Data

[63] Continuation-in-part of Ser. No. 755,982, Dec. 30, 1976, abandoned.

[30] Foreign Application Priority Data

Dec. 28, 1977 [FR] France ............................ 77 39515
Dec. 28, 1977 [JP] Japan ............................ 52-157557
Dec. 29, 1977 [DE] Fed. Rep. of Germany ....... 2758565
Dec. 29, 1977 [NL] Netherlands ...................... 7714564

[51] Int. Cl.$^3$ ............................................. C07C 37/72
[52] U.S. Cl. ............................ 568/724; 568/638; 568/721; 568/725; 568/730; 568/48; 568/34

[58] Field of Search ............. 568/724, 721, 638, 730, 568/725; 260/609 F, 607 AR

[56] References Cited

U.S. PATENT DOCUMENTS

| | | | |
|---|---|---|---|
| 2,959,622 | 11/1960 | Gumme et al. ............... | 568/724 |
| 3,111,544 | 11/1963 | Jous et al. .................... | 568/724 |
| 3,162,690 | 12/1964 | Marx et al. ................... | 568/724 |
| 3,277,183 | 10/1966 | Heller et al. .................. | 568/724 |
| 3,919,330 | 11/1975 | Kwantes et al. .............. | 568/724 |

OTHER PUBLICATIONS

Vogel, "Practical Org. Chem.", 3rd ed. (1957), pp. 122–128.

*Primary Examiner*—Norman Morgenstern
*Attorney, Agent, or Firm*—William F. Mufatti

[57] ABSTRACT

A process for purifying crude diphenols via a water co-solvent system is disclosed.

10 Claims, No Drawings

PROCESS FOR PURIFYING CRUDE DIPHENOLS

This application is a continuation-in-part of copending application Ser. No. 755,982 filed Dec. 30, 1976 now abandoned.

BACKGROUND OF THE INVENTION

It is well known that the purity of diphenols is of paramount importance regarding the quality of polymers which are prepared therefrom. Isomeric diphenols and other impurities specified herein that often accompany the desired p,p'-diphenols are often deleterious since such impurities do not participate as well in and may impede the polymerization processes. It is thus desirable and important to obtain the p,p'-diphenols in their highest purity in order to secure the quality of the polymers which are prepared therefrom. Since isomeric diphenols always accompany the desired p,p'-diphenols, purification of the crude reaction products is always necessary.

Purification of crude mixtures of p,p'-diphenols is often effected by the use of organic solvents such as benzene, methylene chloride or toluene. The use of these and similar solvents results in costly purification due to both the cost of solvents and the relative inefficiency of the method. Another purification method is set forth in U.S. Pat. No. 3,919,330. In this method crude 2,2-bis(4-hydroxyphenyl)propane is dissolved in ethylene glycol and the 2,2-bis(4-hydroxyphenyl)propane is recovered after partial precipitation with water. However, this method requires the use of large amounts of ethylene glycol and the necessity of an additional step of recovering the anhydrous glycol from the aqueous mother liquor in order to reuse it. Furthermore, although this process teaches a method of separating the desired 2,2-bis-(4-hydroxyphenyl)propane from its more soluble isomer, it does not effect removal of the less soluble impurities from the crude product.

DESCRIPTION OF THE INVENTION

It has been found that p,p'-diphenols of high purity can be obtained by the steps of: (a) dispersing the crude p,p'-diphenol in a heated system of water and an alcoholic or phenolic co-solvent or mixtures of co-solvents so that the desired p,p'-diphenol and the impurities that are more soluble than the desired diphenol are dissolved in the system at a temperature that is at or near the boiling point of water or the water/co-solvent system; (b) removing those impurities that are less soluble than the desired diphenol from the system, such as by filtration; and (c) cooling the system to achieve the separation of the desired purified diphenol. The "more soluble" impurities will remain in the aqueous-co-solvent system.

For example, one method to achieve this purification comprises dispersing the crude p,p'-diphenol in water, heating the resulting slurry and then adding a water soluble alcoholic or phenolic co-solvent until the near dissolution of the crude diphenol results, at or near the boiling point of the resulting solvent system. Subsequent filtration of the less soluble impurities, cooling the filtrate and recovery of the recrystallized solids yields p,p'-diphenols of improved purity (assay).

Alternatively, the crude diphenols are heated with a premixed water and co-solvent mixture, with stirring, until near dissolution of the crude diphenol results, followed by filtration of the less soluble impurities, cooling the filtrate and subsequent recovery of the recrystallized solid purified p,p'diphenol.

The term "near dissolution", as used herein, refers to the dissolution of the desired p,p'-diphenol and any impurities that are more soluble (in the water/co-solvent system) than the desired p,p'-diphenol, leaving undissolved those impurities that are less soluble, in the water/co-solvent system, than the desired diphenol. Depending on the needs of the individual practitioner of this invention, such as the particular p,p'-diphenol which is to be purified, the desired degree of purification of the p,p'-diphenol and considerations such as of both time and expense, it is understood that a skilled practitioner may choose to have less than 100% of the desired p,p'-diphenol dissolved in the water/co-solvent system.

The terms "alcoholic or phenolic" co-solvents as used herein refers to monohydroxylic compounds; i.e., alcohols or phenols that have only one hydroxy (—OH) function, including, but not limited to, ether-alcohols, aminoalcohols, ketoalcohols, phenols, aliphatic alcohols, cycloaliphatic alcohols, and the like. Examples of these water soluble alcoholic or phenolic co-solvents include methanol, ethanol, 1-propanol, 2-propanol, tertiary butyl alcohol, 2-aminoethanol (ethanolamine), 2-methoxyethanol, 4-hydroxy-4-methyl-2-pentanone, phenol, etc. and mixtures thereof. Also, one or more of these alcoholic or phenolic co-solvents and water may be employed concurrently to accomplish recrystallization.

The amount of water soluble alcoholic or phenolic co-solvent employed herein is dependent upon the amount of water used in the recrystallization, in that the larger the amount of water per solute, the greater the amount of co-solvent that will be required.

Generally, after completion of the addition of the alcoholic or phenolic co-solvent to the slurry of water-crude p,p'-diphenol, the weight ratio of co-solvent to the water-crude p,p'-diphenol is from about 10:100 to about 40:100.

A wide variety of diphenols may be purified according to the method of the instant invention. The preferred diphenols include 2,2-bis(4-hydroxyphenyl)propane, 4,4'-thiodiphenol, 4,4'-oxydiphenol, cyclohexylidenediphenol, p,p'-biphenol, 2,2-bis(3,5-dimethyl-4-hydroxyphenyl)propane, as well as the corresponding tetrachloro and tetrabromo analogs, p,p'-sulfonyldiphenol, bis-(3,5-dimethyl-4-hydroxyphenyl sulfone), and the like. The preferred diphenol, 2,2-bis(4-hydroxyphenyl)propane consists, in its crude state, of a mixture of the p,p' and o,p' isomers and a host of other impurities. Some of these impurities, such as the o,p' isomer, are more soluble than the p,p' isomer in the water/co-solvent system and some are less so. It is, therefore, a feature of this invention to add to the aqueous slurry of the crude reaction mixtures just enough co-solvent that is necessary for the dissolution of the o,p' and p,p' isomer content of the mixture, leaving the lesser soluble components undissolved. The latter are conveniently removed by filtration. Subsequent cooling of the filtered solution deposits the less soluble p,p' isomer, leaving much or all of the more soluble o,p' isomer and other more soluble components in solution.

The term "more soluble impurities" as used in the specification and claims refers to those impurities that are more soluble, in the water/co-solvent system, than the desired p,p'-diphenol. The term "less soluble impurities" as used in the specification and claims refers to those impurities that are less soluble, in the water/co-solvent system, than the desired p,p'-diphenol.

The temperature at which the instant purification method is conducted should be above ambient. The maximum temperature is not critical, although sometimes it is determined by the boiling point of the lowest boiling co-solvent. When working at atmospheric pressure, it is desirable to stay near about 90° C. to 100° C., so that the solvent properties of water can be best utilized. Since the solubility of diphenols increases dramatically with temperature, it is often advantageous to use super-atmospheric pressure, such as those obtained by pressurizing the recrystallization vessels by inert gases or by employing autogeneous pressures. In some cases, 150° C. or even higher temperatures are preferable, such as those available by the use of superheated steam.

It was found that the use of aqueous solvents results usually in the formation of well developed larger crystals of the desired purified product, which can be readily separated by filtration. In the case of 2,2-bis(4-hydroxyphenyl)propane, the crystals have the rhombic crystal structure which may have on their surfaces a contamination of the more soluble isomeric impurities, usually the o,p' isomer. A simple slurrying or rinsing of these crystals by a proper solvent, such as methylene chloride, readily removes the impurities and leaves behind the rhombic crystals of the pure p,p' isomers. Similar situations exist with a number of analogous diphenols.

DESCRIPTION OF THE PREFERRED EMBODIMENT

The following examples are set forth to illustrate more clearly the invention to those skilled in the art. Unless otherwise specified, where parts or percents are mentioned, they are parts or percents by weight.

EXAMPLE I

To a one-liter, three-necked flask, equipped with a stirrer, reflux condenser, addition funnel and thermometer, there was charged 50 grams of 2,2-bis(4-hydroxyphenyl)propane (bisphenol-A) and 500 ml. of water and the resultant slurry was heated with the aid of a heating mantle. When the water started to reflux, pure ethanol was gradually added to the aqueous heterogeneous liquid while maintaining a gentle reflux. It required 102.3 grams of the co-solvent ethanol to dissolve the desired diphenol isomer and the more soluble impurities. The less soluble impurities were filtered from the system. Upon cooling to ambient temperature, well developed rhomboid crystals of p,p'-bisphenol-A separated out and were isolated by filtration in nearly quantitative yield.

EXAMPLES II to VI

The procedure of Example I was repeated, except that ethanol was replaced with the co-solvents and in the amounts shown below.

Co-solvents Required to Dissolve the p,p' and o,p' Isomers Present in 50 Grams of Crude Bisphenol-A in 500 Grams of Water at 100° C.

| Example | Co-solvent | Amount of Co-solvent (grams) |
| --- | --- | --- |
| II | 2-Methoxyethanol | 99.4 |
| III | 4-Hydroxy-4-methyl-2-pentanone | 67.3 |
| IV | Phenol | 150.6 |
| V | Ethanolamine | 64.9 |
| VI | Triethanolamine | 94.3 |

EXAMPLE VII

The procedure of Example I was repeated exactly, except that 4,4'-thiodiphenol was used in place of bisphenol-A. The amount of 2-methoxyethanol used to effect the aqueous recrystallization was 62.5 grams.

EXAMPLE VIII

The procedure of Example I was repeated, except the co-solvent utilized was an equal weight part mixture of the co-solvents of Examples I through VI. Enough co-solvent was added to the hot water emulsion of crude BPA to dissolve the p,p'-bisphenol-A and more soluble impurities. The undissolved portion was filtered off. The filtrate was cooled and the purified bisphenol-A was recovered by filtration. Table I sets forth the composition of the crude bisphenol-A and the purified product.

TABLE I

| Component | Crude Bisphenol-A (Wt. %) | Purified Product (Wt. %) |
| --- | --- | --- |
| p,p'-BPA[a] | 97.169 | 98.962 |
| o,p'-BPA[b] | 0.260 | 0.106 |
| Chroman-I[c] | 0.619 | 0.298 |
| Spiro-diphenol[d] | 1.417 | 0.376 |
| IPP-linear-dimer[e] | 0.535 | 0.258 |

[a] 2,2-bis(4-hydroxyphenyl)propane
[b] 2-(2-hydroxyphenyl)-2-(4-hydroxyphenyl)propane
[c] p-(2,2,4-trimethyl-4-chromanyl)phenol
[d] 6,6'-dihydroxy-3,3,3',3'-tetramethyl-1,1'-spirobiindane
[e] 4-methyl-2,4-bis(p-hydroxyphenyl)-1-pentene Obviously, other modifications and variations of the present invention are possible in the light of the above teachings. It is therefore to be understood that changes may be made in the particular embodiments of the invention described which are within the full intended scope of the invention.

What is claimed is:

1. A process for purifying crude diphenols to recover the p,p'-diphenol isomer which comprises (a) dispersing the crude diphenol in a system of water and a monohydroxylic alcoholic or phenolic co-solvent or mixtures of co-solvents so that the p,p'-diphenol and the more soluble impurities are dissolved in the system at a temperature that is at or near the boiling point of water or at or near the boiling point of the water/co-solvent system; (b) removing the less soluble impurities from the system; and (c) cooling the system to achieve the separation of the purified p,p'-diphenol.

2. A process according to claim 1 wherein the co-solvent is selected from the group consisting of methanol, ethanol, 1-propanol, 2-propanol, 2-methoxyethanol and ethanolamine.

3. A process according to claim 1 wherein crude diphenol is crude 2,2-bis(4-hydroxyphenyl)propane.

4. A process according to claim 1 wherein, in step (a), the water/co-solvent system is at a temperature of from about 90° C. to 100° C. at atmospheric pressure.

5. A process according to claim 1 wherein step (a) is carried out at super-atmospheric pressure.

6. A process for purifying crude diphenols to recover the p,p'-diphenol isomer which comprises (a) dispersing the crude diphenol in water; (b) heating the resulting slurry; (c) adding a monohydroxylic alcoholic or phenolic co-solvent to the slurry so that the p,p'-diphenol and the more soluble impurities are dissolved in the resulting water/co-solvent system at a temperature that is at or near the boiling point of water or at or near the boiling point of the water/co-solvent system; (d) removing the less soluble impurities from the system; and (e) cooling the system to achieve the separation of the purified p,p'-diphenol.

7. A process according to claim 6 wherein the co-solvent is selected from the group consisting of methanol, ethanol, 1-propanol, 2-propanol, 2-methoxyethanol and ethanolamine.

8. A process according to claim 6 wherein crude diphenol is crude 2,2-bis(4-hydroxyphenyl)propane.

9. A process according to claim 6 wherein, in step (c), the water/co-solvent system is at a temperature of from about 90° C. to 100° C. at atmospheric pressure.

10. A process according to claim 7 wherein step (c) is carried out at super-atmospheric pressure.

* * * * *